(12) United States Patent
Saindane et al.

(10) Patent No.: US 6,500,917 B1
(45) Date of Patent: Dec. 31, 2002

(54) PROCESS FOR THE PREPARATION OF POLYETHER PHOSPHATES

(75) Inventors: Manohar Tukaram Saindane, Collegeville, PA (US); David Lee Ladd, Wayne, PA (US)

(73) Assignee: Amersham Health AS, Oslo (NO)

( * ) Notice: Subject to any disclaimer, the term of this patent is extended or adjusted under 35 U.S.C. 154(b) by 0 days.

(21) Appl. No.: 09/489,831

(22) Filed: Jan. 24, 2000

Related U.S. Application Data (63) Continuation of application No. PCT/GB98/02231, filed on Jul. 24, 1998.
(60) Provisional application No. 60/053,838, filed on Jul. 25, 1997.

(30) Foreign Application Priority Data

Jul. 25, 1997 (GB) .............................. 9715770

(51) Int. Cl.[7] .............................. C08G 79/02; C07F 9/02
(52) U.S. Cl. .................... 528/400; 558/186; 987/228
(58) Field of Search .................... 558/186; 987/228; 528/400, 399

(56) References Cited

U.S. PATENT DOCUMENTS

| 3,032,578 A | * | 5/1962 | Mac Mullen | 558/186 |
|---|---|---|---|---|
| 3,294,873 A | | 12/1966 | Lutz et al. | |
| 3,422,166 A | * | 1/1969 | Davis | 558/186 |
| 3,462,520 A | | 8/1969 | Nehmsmann et al. | |
| 3,556,825 A | | 1/1971 | Lynch | |
| 3,666,843 A | * | 5/1972 | Fearing | 558/186 |
| 5,372,743 A | * | 12/1994 | Miyamoto et al. | 558/186 |
| 5,944,650 A | * | 8/1999 | Hu et al. | 558/186 |

FOREIGN PATENT DOCUMENTS

| WO | WO 94 21240 A | 9/1994 |
|---|---|---|
| WO | WO 96 13508 A | 5/1996 |

* cited by examiner

*Primary Examiner*—Philip Tucker
(74) *Attorney, Agent, or Firm*—Royal N. Ronning, Jr.; Robert F. Chisholm (57) ABSTRACT

The invention provides an improved process for the synthesis of compounds carrying at least one phosphate group, especially polyalkylene glycol phosphate compounds, said process comprising the steps of: (a) reacting a compound containing at least one primary alcohol moiety with a diaryl- or diaralkyl-halophosphate whereby to form the corresponding diaryl- or diaralkyl-phosphate ester; (b) reductively cleaving the resulting product; and (c) if desired, repeating steps (a) and (b) with the product of step (b) whereby to produce a compound carrying two or more phosphate groups. Advantages of the process in accordance with the invention are that this avoids the production of by-products and results in products which are low in impurities. Also provided are novel diaryl- and diaralkyl-phosphate ester compounds, in particular polyethylene glycol diphenylphosphate ester and derivatives thereof.

26 Claims, 7 Drawing Sheets

PROCESS FOR THE PREPARATION OF POLYETHER PHOSPHATES

This application is a continuation of pending international application number PCT/GB98/02231 filed Jul. 24, 1998 (of which the entire disclosure of the pending, prior application is hereby incorporated by reference), which itself is a continuation-in-part of U.S. provisional application No. 60/053,838 filed Jul. 25, 1997.

The present invention relates to an improved process for the preparation of compounds carrying one or more phosphate groups and to intermediates therefor. In particular, the invention relates to a process for the preparation of polyalkylene glycol phosphates.

Surface active compositions comprising phosphate esters of alkoxylated alcohols are known and described, for example in U.S. Pat. No. 3,462,520. Bis-diphenyl phosphate derivatives of certain alkylene glycols for use in producing flame retardant rayon are described in U.S. Pat. No. 3,556,825. U.S. Pat. No. 3,294,873 discloses phosphorylated polyether polyols and flame-retardant polyurethane compositions derived therefrom.

Recently it has been suggested that the blood residence time of parenterally administered magnetic particles for use in MR imaging may be prolonged by chemical binding of a stabiliser substance to the magnetic particle surface (see e.g. U.S. Pat. No. 5,160,725 and WO-A-94/21240).

Examples of materials which may be used as stabilisers include carbohydrates such as oligo- and polysaccharides, polyamino acids, oligo- and polynucleotides and polyalkylene oxides. Such substances must have at least one chemically reactive functional group, such as a carboxyl, phosphate or phosphonate group, by means of which they are able to bond chemically or adsorb to the surface of the magnetic particles. In this regard, functionalised polymers, such as functionalised polyalkylene oxides, have proved particularly useful.

Organic mono- and di-phosphates are one group of compounds which are capable of forming chemical bonds with the surface of magnetic particles and which have thus been proposed for use as stabiliser substances (see e.g. U.S. Pat. No. 5,160,725). One compound which has been widely suggested for use as a stabiliser substance is a phosphorus oxide terminal polyethylene glycol, in particular, methoxy-polyethylene glycol phosphate (hereinafter referred to as methoxy-PEG-phosphate or MPP).

In the industrial manufacture of polyethylene glycol phosphate, it is important to reduce the production of undesirable by-products and to optimise the yield and purity of the final product. This in turn can lead to a substantial reduction in production costs.

We have now developed an improved process for the synthesis of compounds carrying one or more phosphate groups, especially polyalkylene glycol phosphate compounds, which process avoids the production of by-products and so greatly increases the yield. The products produced by such a process are also low in impurities.

Thus, viewed from one aspect the invention provides a process for the preparation of a compound carrying a phosphate group, said process comprising the steps of:
  (a) reacting a compound containing at least one primary alcohol moiety with a diaryl- or diaralkyl-halophosphate whereby to form the corresponding diaryl- or diaralkyl-phosphate ester;
  (b) reductively cleaving the resulting product; and
  (c) if desired, repeating steps (a) and (b) with the product of step (b) whereby to produce a compound carrying two or more phosphate groups.

The process in accordance with the invention is conveniently a two-step process comprising steps (a) and (b) as defined above in which high yields are obtained by conducting the first reaction step under especially mild conditions.

By repeating steps (a) and (b) with the product of step (b), compounds carrying two, three or more phosphate moieties can, however, be prepared. In this way, the process of the invention can be used to prepare polymers of phosphates such as diphosphate, triphosphate and polyphosphates. Such oligo- and polyphosphates are particularly preferred for use as stabiliser substances since these are capable of binding more strongly to magnetic particles due to the presence of multiple binding sites.

Compounds containing at least one primary alcohol moiety for use in the process of the invention include alcohols having a molecular weight of at least 50, especially preferably of at least 100. Hydrophilic alcohols are particularly preferred.

Particularly preferred compounds containing at least one primary alcohol moiety include long chain polymers, such as polyalkylene oxide compounds having a molecular weight (weight average) in the range of from 100 to 200,000, preferably from 250 to 100,000, more preferably from 250 to 20,000, e.g. from 500 to 3,000.

Polyalkylene oxides suitable for use in the process of the invention may be linear or branched, preferably linear. Preferred polyalkylene oxides include polyethylene oxides, polypropylene oxides, polybutylene oxides and derivatives thereof. Particularly preferred polyalkylene oxides include polyethylene oxides, polypropylene oxides and random and block copolymers thereof. Conveniently, the number of polyethylene oxide and polypropylene oxide groups in such compounds may be from 1 to 300, preferably from 2 to 100.

Preferred derivatives of polyalkylene oxides for use in the process of the invention include the $C_{1-8}$ straight-chain or branched alkoxy, preferably $C_{1-6}$ alkoxy, e.g. methoxy substituted compounds.

Particularly preferably, the compound containing at least one primary alcohol moiety for use in the process of the invention is methoxy polyethylene glycol (hereinafter referred to as methoxy-PEG).

The compound carrying at least one primary alcohol moiety is preferably reacted with an equivalent molar concentration of a diaryl- or diaralkyl-halophosphate compound, particularly preferably with an equivalent molar concentration of a diaryl halophosphate compound. Whilst the diaryl- or diaralkyl-halophosphate compound for use in the process of the invention is preferably a diaryl- or diaralkyl-chlorophosphate, other diaryl- or diaralkyl-halophosphates may be used, e.g. diaryl- or diaralkyl-iodophosphates and bromophosphates.

As used herein, "aralkyl" is intended to include alkyl groups substituted by at least one aryl group, preferably an alkyl group substituted by a single aryl group.

As used herein, "aryl" is intended to include aromatic groups containing from 5 to 12, preferably those containing 5 or 6 ring atoms, optionally substituted by one or more halogen atoms and/or nitro groups, or by one or more groups selected from R, OR, SR, NHR, $NR_2$, $CO_2R$ and CONHR in which each R independently represents a hydrogen atom or an alkyl group.

In the compounds for use in the process of the invention, any alkyl moiety, unless otherwise specified, may be straight-chained or branched and preferably contains from 1 to 8, more preferably from 1 to 6, especially preferably from 1 to 4 carbon atoms.

Aryl groups suitable for use in the invention include heterocyclic aryl groups having one or more heteroatoms selected from oxygen, nitrogen and sulphur.

Preferred aryl groups include phenyl and naphthyl.

Particularly preferred diaryl halophosphate compounds for use in step (a) include diphenyl iodophosphate, diphenyl bromophosphate and diphenyl chlorophosphate. Diphenyl chlorophosphate is especially preferred.

Preferred diaralkyl halophosphates for use in step (a) include dibenzyl halophosphates, e.g. dibenzyl iodophosphate, dibenzyl bromophosphate and dibenzyl chlorophosphate. Particularly preferred is dibenzyl chlorophosphate. Other diaralkyl halophosphates which may be used in step (a) include di-4-nitrobenzyl halophosphates, e.g. di-4-nitrobenzyl chlorophosphate.

Conveniently step (a) may be carried out in a solvent or mixture of solvents selected from methylene chloride, methanol, ethanol, acetone, diethylether, methylformamide, dimethylformamide, dimethylsulphoxide, benzene, chlorobenzene, tetrahydrofuran and dioxane. It is particularly advantageous to carry out step (a) in the presence of methylene chloride. The reaction may, however, be carried out without a solvent.

Preferably, step (a) is also carried out in the presence of an organic base, or mixture of organic bases, which may simultaneously act as a solvent. Examples of organic bases suitable for use in the process of the invention include triethylamine, N,N-diisopropylethylamine, pyridine and dimethyl-aminopyridine or mixtures thereof. A particularly preferred mixture of organic bases for use in step (a) is a mixture of triethylamine and dimethylaminopyridine.

Step (a) may be conducted at temperatures in the range of from 0 to 35° C., preferably at temperatures from 20 to 25° C. In general, ambient temperature is preferred.

Step (b) involves reductive cleavage of the aryl or aralkyl groups from the diaryl- or diaralkyl-phosphate ester compound produced in step (a). This is conveniently carried out hydrogenolytically at temperatures of from 25 to 50° C., preferably from 38 to 45° C., e.g. from 40 to 42° C., preferably at a pressure of from 200 to 450 kPa, e.g. from 300 to 350 kPa.

Hydrogenation is preferably carried out using platinum oxide (Adam's catalyst) at a temperature of 40° C. and a pressure of 350 kPa. Other hydrogenation catalysts suitable for use in step (b) include palladium or platinum on charcoal.

Step (b) is preferably carried out in the presence of at least one protic solvent. Suitable protic solvents for use in step (b) are those which result in the minimal production of by-products and include organic acids, such as acetic acid, isopropanol and methanol. Acetic acid is particularly preferred. Alternatively, step (b) may be carried out in the absence of any solvent.

In carrying out steps (a) and (b) any reactive groups present, especially on the compound carrying the primary alcohol moiety, may be protected during the reaction using conventional protecting groups which may be cleaved by conventional procedures, e.g. hydrolysis, at the end of the reaction.

Conveniently, the compounds produced in accordance with the process of the invention are isolated by conventional work-up procedures and, optionally, further purified using procedures well known in the art, such as for example re-crystallisation from a solvent mixture, e.g. from tetrahydrofuran/hexanes. Other solvents which may be used in this regard include acetone, ethanol/hexanes and ethyl acetate/hexanes.

Step (a) results in the formation of a diaryl- or diaralkyl-phosphate ester compound, e.g. a diphenyl phosphate ester, which may be isolated and, if desired, further purified using conventional purification procedures. Such compounds form a further aspect of the invention.

Viewed from a further aspect the invention thus provides diaryl- and diaralkyl-phosphate ester compounds. Preferred compounds in accordance with the invention include those of formula I:

$$R^1O\text{—}PO(OR^2)_2 \qquad (I)$$

(wherein $R^1$ is the residue of a polyalkylene oxide having a weight average molecular weight in the range of from 100 to 200,000, preferably from 250 to 100,000, more preferably from 250 to 20,000, e.g. from 500 to 3,000; and $R^2$ is an aralkyl, or more preferably an aryl moiety as hereinbefore defined).

Preferably, $R^2$ is phenyl or naphthyl, particularly preferably phenyl.

Particularly preferred compounds in accordance with the invention include polyethylene glycol diphenylphosphate ester and derivatives thereof, e.g. methoxy polyethylene glycol diphenylphosphate ester.

Viewed from a yet further aspect, the invention provides a product, e.g. a compound carrying one or more phosphate groups prepared by the process hereinbefore described, and a magnetic particle, particularly preferably a superparamagnetic particle, linked to one or more of such products.

Particularly preferred compounds prepared in accordance with the process of the invention include polyethylene glycol derivatives, such as mono- and di-PEG-phosphate and alkoxy-PEG phosphates, e.g. methoxy-PEG-phosphate, methoxy-PEG-diphosphate and methoxy-PEG-triphosphate.

The process in accordance with the invention results in minimal production of undesirable by-products and a yield of the desired product in the range of from 90 to 95% by weight. Conveniently, the product produced in accordance with the process of the invention has a purity in excess of 95% by weight, preferably greater than 98% by weight.

The invention will now be further described with reference to the following non-limiting Examples and the accompanying Figures in which.

BRIEF DESCRIPTION OF THE DRAWINGS

EXAMPLE 1

MeO—PEG—OH + Diphenyl Chlorophosphate ----→

MeO—PEG—O—P(=O)(OPh)—OPh

MeO—PEG—O—P(=O)(OPh)—OPh ----→ MeO—PEG—O—P(=O)(OH)—OH (MPP)

(a) Methoxy polyethyleneglycol diphenylphosphate (Mol. Wt. 2000)

To an inerted 3 liter flask was charged 100 g methoxy polyethylene glycol (mol. wt. 2000) and 600 ml methylene chloride. The mixture was stirred for 1 hour at ambient temperature to obtain a solution. 8 g triethylamine and 9.7 g 4-dimethylaminopyridine was then added and stirred for 30 minutes. A solution of 20 g diphenyl chlorophosphate in 50 ml methylene chloride was added dropwise over a period of 30 minutes. After the addition was complete the resulting mixture was stirred at ambient temperature for 20 hours.

The reaction mixture was quenched with 500 ml 1N hydrochloric acid and stirred for 30 minutes. The organic layer was separated and washed once with 500 ml 1N hydrochloric acid and then with 500 ml water. It was then dried over anhydrous sodium sulphate and the solvent was removed by distillation at atmospheric pressure to give a colourless oil. This oily residue was dissolved in 200 ml THF and 200 ml hexanes at 40–45° C. and slowly cooled to 5–10° C. over a period of 1 hour. A further 200 ml hexanes was added and the precipitated white solid was collected by filtration and washed with 200 ml hexanes. Vacuum drying at ambient temperature for 24 hours afforded 109 g (97%) of the title compound.

Figure 1:
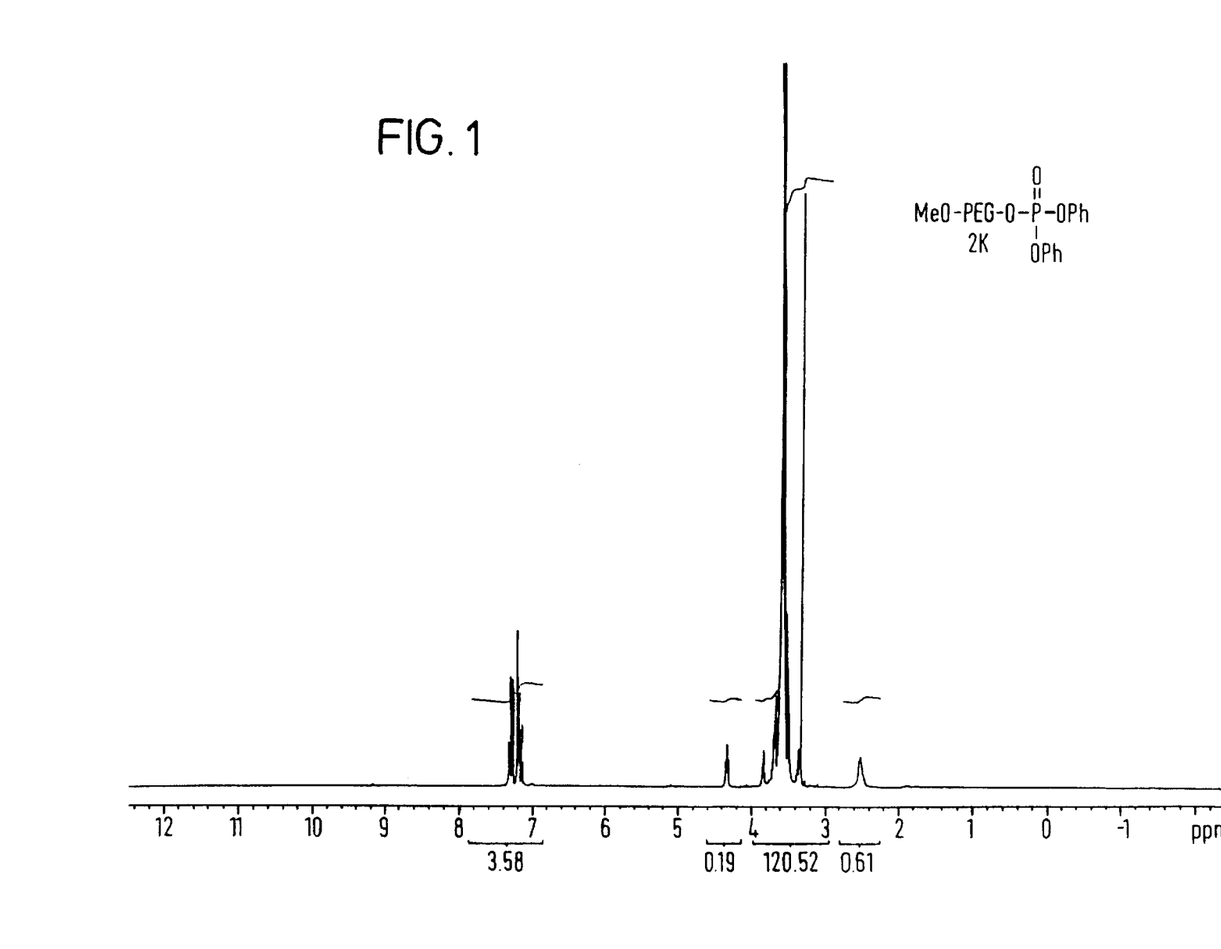
FIGS. 1 and 4 are $^1$H NMR spectra taken at 7.0463T with deuterated chloroform as a solvent.
Figure 2:
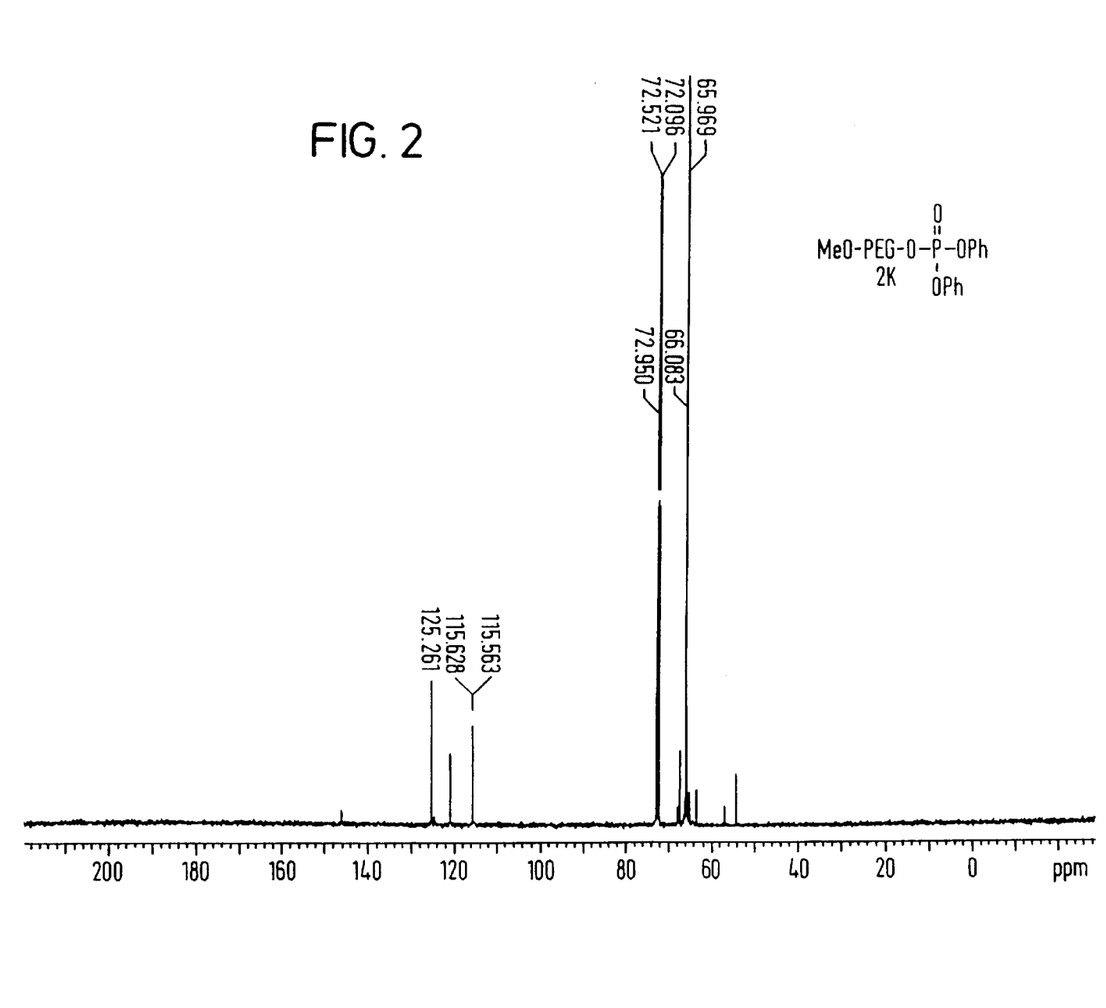
FIGS. 2 and 5 are $^{13}$C NMR spectra taken at 7.0463T with deuterated chloroform as a solvent.
Figure 3:
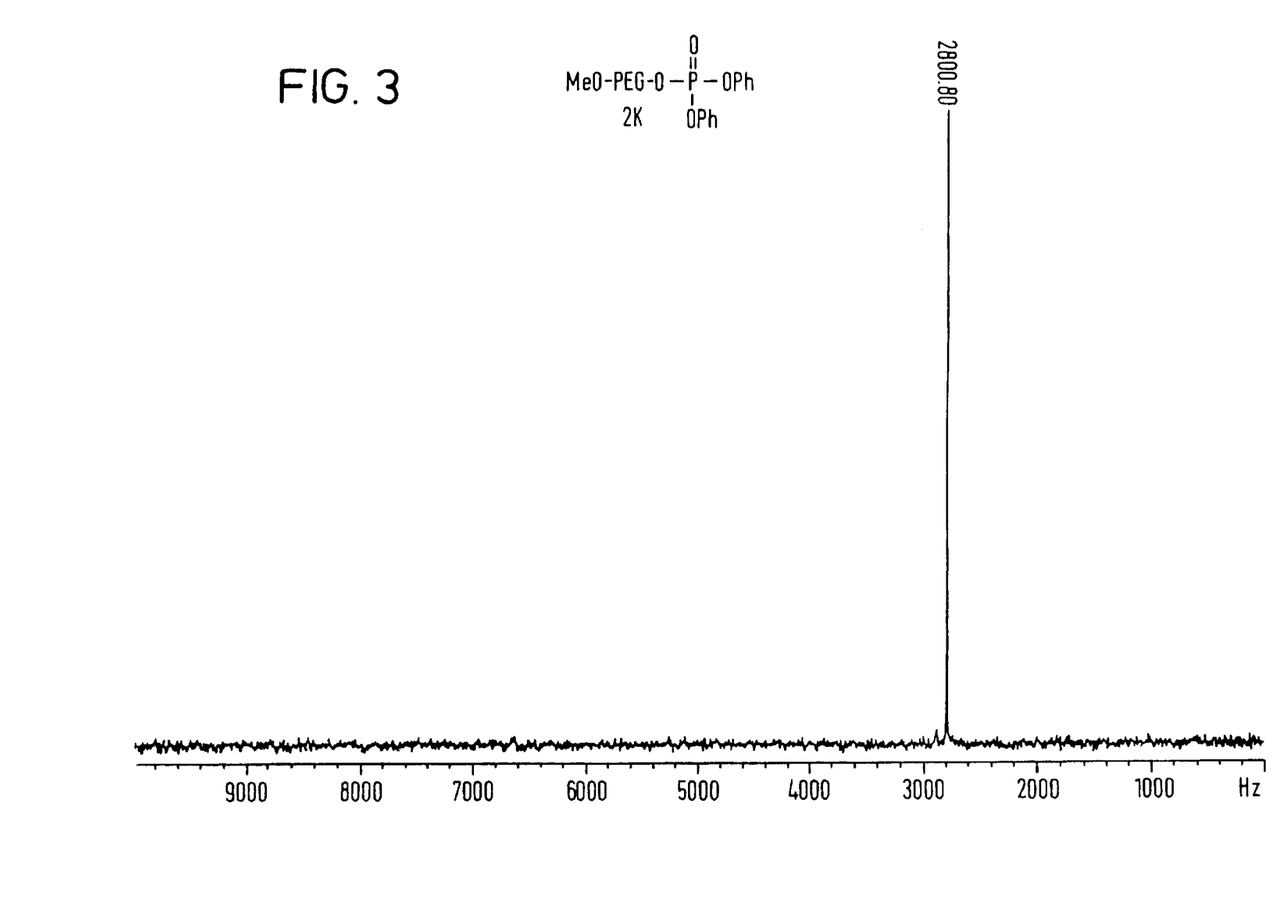
FIGS. 3 and 6 are $^{31}$P NMR spectra taken at 9.3950T with deuterated chloroform as a solvent.
Figure 4:
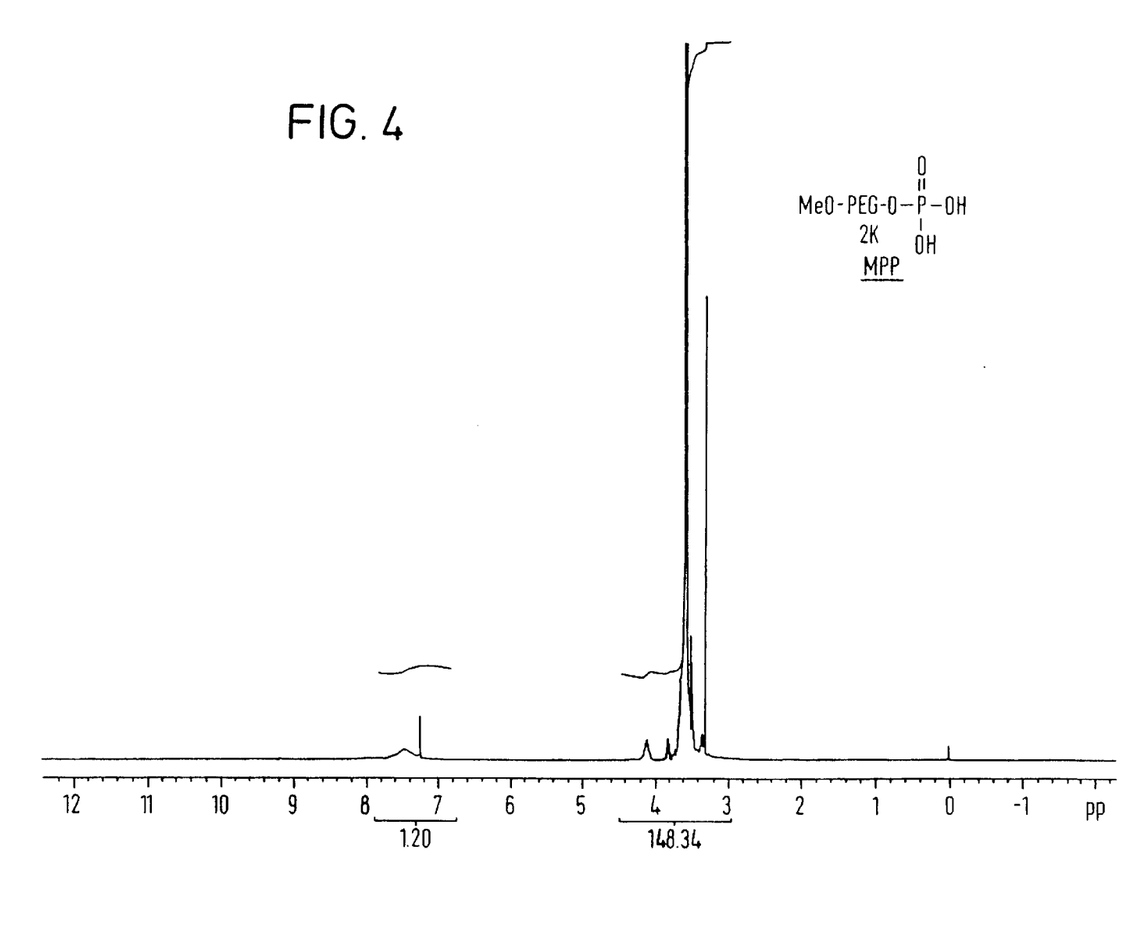
Figure 5:
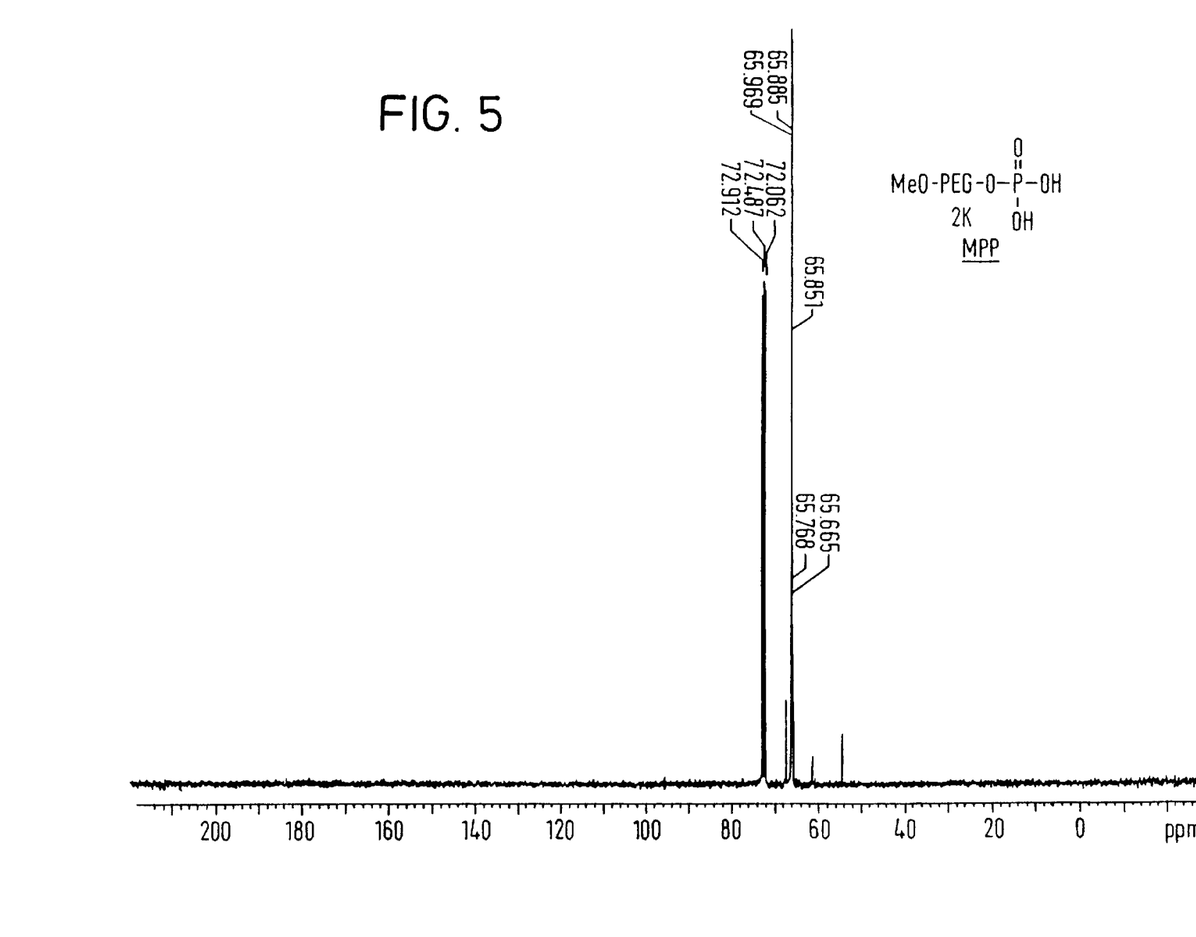
Figure 6:
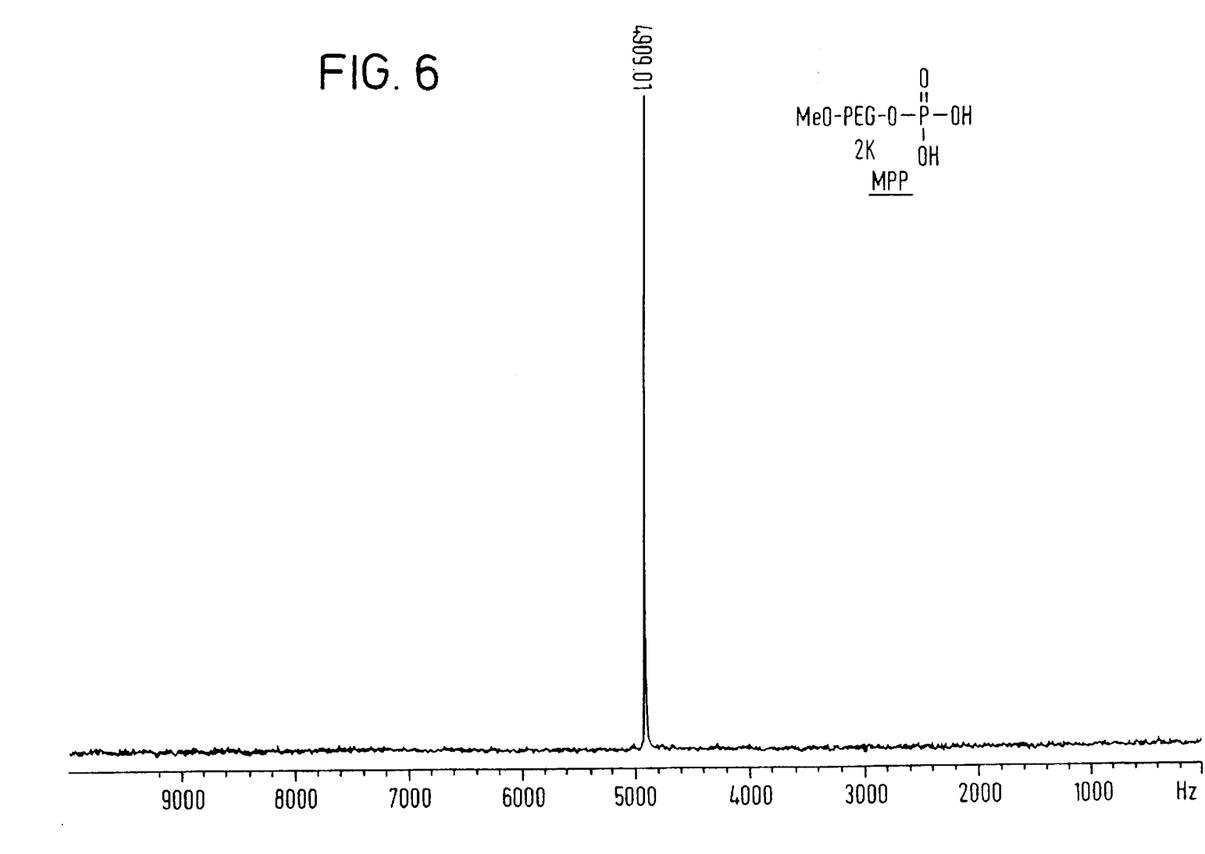
Figure 7:
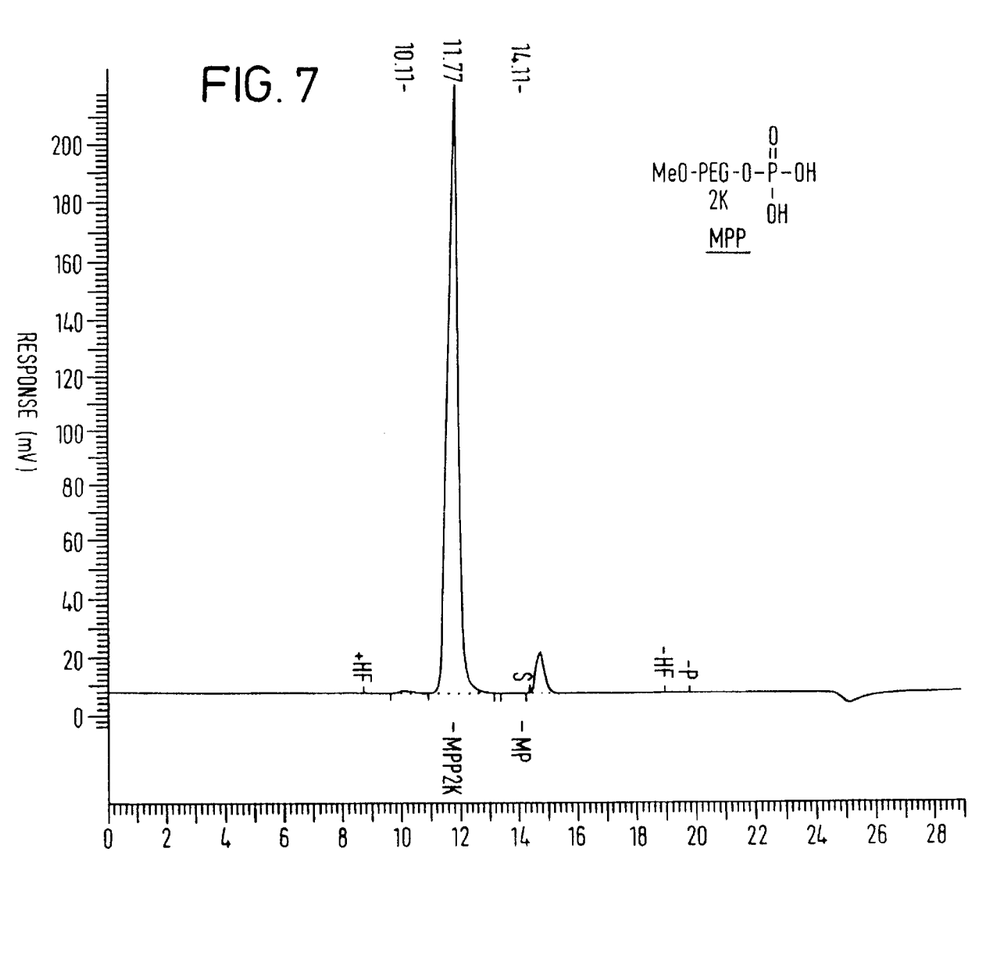
FIG. 7 is a chromatogram obtained using size exclusion chromatography in which a sample of approximately 10 mg/mL in 5 mM $NaH_2PO_4$, pH 7 buffer (mobile phase) is chromatographed using a TSK-Gel column. Detection is by refractive index. Quantification is performed on the basis of an external methoxy poly(ethylene glycol)phosphate, MW 2,000 standard.

This material was characterised by $^1$H, $^{13}$C and $^{31}$P NMR spectroscopy (see attached FIGS. 1 to 3).

(b) Methoxy polyethylene glycol phosphate (Mol. Wt. 2000)

To a solution of 100 g methoxy polyethylene glycol diphenylphosphate in 1 liter of acetic acid was added 3.0 g Adam's catalyst. The mixture was then hydrogenated in a stirred autoclave at 40° C. and 350 kPa pressure for a period of 20–24 hours. The catalyst was then removed by filtration and the filtrate concentrated under vacuum at a temperature below 50° C. to give a colourless oil. This oily residue was then dissolved in 400 ml THF at 40° C. and then cooled to 10° C. over a period of 30 minutes. The slurry was then diluted with 400 ml hexanes and stirred for 30 minutes at 5–10° C. The resulting white solid was collected by filtration and washed with 400 ml hexanes. It was then dried at ambient temperature under vacuum for 48 hours to yield 90 g (98%) of the title compound.

The material was characterised by $^1$H, $^{13}$C and $^{31}$P NMR, GPC and phosphate group titration assay (see attached FIGS. 4 to 7).

What is claimed is:

1. A process for the preparation of a compound carrying a phosphate group, said process comprising the steps of:
   (a) reacting a compound containing at least one primary alcohol moiety with a diaryl- or diaralkyl- halophosphate in which said aryl group is an aromatic carbocyclic or heterocyclic group whereby to form the corresponding diaryl- or diaralkyl-phosphate ester;
   (b) reductively cleaving said aryl or aralkyl groups from the resulting product; and
   (c) if desired, repeating steps (a) and (b) with the product of step (b) whereby to produce a compound carrying two or more phosphate groups.

2. A process as claimed in claim 1 wherein said diaryl- or diaralkyl-halophosphate compound is a diaryl- or diaralkyl-chlorophosphate.

3. A process as claimed in claim 2 wherein said diaryl halophosphate compound is diphenyl iodophosphate, diphenyl bromophosphate or diphenyl chlorophosphate.

4. A process as claimed in claim 2 wherein said diaralkyl halophosphate compound is dibenzyl iodophosphate, dibenzyl bromophosphate, dibenzyl chlorophosphate or di-4-nitrobenzyl chlorophosphate.

5. A process as claimed in claim 1 wherein said compound carrying at least one primary alcohol moiety is a polyalkylene oxide having a weight average molecular weight in the range of from 100 to 200,000.

6. A process as claimed in claim 5 wherein said polyalkylene oxide is a polyethylene oxide, polypropylene oxide, polybutylene oxide or a derivative thereof.

7. A process as claimed in claim 6 wherein said polyalkylene oxide carries at least one $C_{1-8}$ straight-chain or branched alkoxy group.

8. A process as claimed in claim 7 wherein said polyalkylene oxide is methoxy polyethylene oxide.

9. A process as claimed in claim 1 wherein step (a) is effected in the presence of a solvent selected from methylene chloride, methanol, ethanol, acetone, diethylether, methylformamide, dimethylformamide, dimethylsulphoxide, benzene, chlorobenzene, tetrahydrofuran, dioxane and mixtures thereof.

10. A process as claimed in claim 1 wherein step (a) is effected in the presence of an organic base selected from triethylamine, N,N-diisopropylethylamine, pyridine, dimethyl-aminopyridine and mixtures thereof.

11. A process as claimed in claim 1 wherein step (a) is carried out at a temperature in the range of from 0 to 35° C.

12. A process as claimed in claim 1 wherein step (b) is carried out hydrogenolytically at a temperature of from 25 to 50° C.

13. A process as claimed in claim 12 wherein hydrogenation is carried out at a pressure of from 200 to 450 kPa.

14. A process as claimed in claim 12 wherein hydrogenation is carried out in the presence of a catalyst selected from platinum oxide and palladium or platinum on charcoal.

15. A process as claimed in claim 1 wherein step (b) is effected in the presence of at least one protic solvent.

16. A process as claimed in claim 15 wherein said solvent is acetic acid, isopropanol or methanol.

17. A process as claimed in claim 1 wherein the yield of the product from step (b) and/or step (c) is from 90 to 95% by weight.

18. A compound of formula I:

$$R^1O\text{—}PO(OR^2)_2 \qquad (I)$$

wherein $R^1$ is the residue of a $C_{1-8}$ straight-chain or branched alkoxy substituted polyalkylene oxide having a weight average molecular weight in the range of from 100 to 200,000; and $R^2$ is an aryl or aralkyl moiety and wherein aryl is an aromatic carbocyclic or heterocyclic group.

19. A compound as claimed in claim 18 wherein said compound is methoxy polyethylene glycol diphenylphosphate ester.

20. A process as claimed in claim 3 wherein said diaryl halophosphate compound is diphenyl chlorophosphate.

21. A process as claimed in claim 4 wherein said diaralkyl halophosphate compound is dibenzyl chlorophosphate.

22. A process as claimed 5 wherein said compound carrying at least one primary alcohol moiety is a polyalkylene oxide having a weight average molecular weight in the range of from 500 to 3,000.

23. A process as claimed in claim 11 wherein step (a) is carried out at a temperature in the range of from 20 to 25° C.

24. A process as claimed in claim 12 wherein step (b) is carried out hydrogenolytically at a temperature of from 40 to 42° C.

25. A process as claimed in claim 16 wherein said solvent is acetic acid.

26. A compound of formula I:

$$R^1O\text{---}PO(OR^2)_2 \qquad (I)$$

wherein $R^1$ is the residue of a $C_{1-8}$ straight-chain or branched alkoxy substituted polyalkylene oxide having a weight average molecular weight in the range of from 500 to 3,000; and $R^2$ is an aryl or aralkyl moiety as defined in claim 18.

* * * * *